United States Patent
Masubuchi

(10) Patent No.: US 9,662,236 B2
(45) Date of Patent: May 30, 2017

(54) STENT DELIVERY SYSTEM

(71) Applicant: TERUMO KABUSHIKI KAISHA, Shibuya-ku (JP)

(72) Inventor: Yuki Masubuchi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 74 days.

(21) Appl. No.: 14/035,336

(22) Filed: Sep. 24, 2013

(65) Prior Publication Data

US 2014/0025155 A1    Jan. 23, 2014

Related U.S. Application Data

(63) Continuation of application No. PCT/JP2012/051296, filed on Jan. 23, 2012.

(30) Foreign Application Priority Data

Mar. 25, 2011    (JP) .................................. 2011-66847

(51) Int. Cl.
*A61F 2/962*    (2013.01)

(52) U.S. Cl.
CPC ..................... *A61F 2/962* (2013.01)

(58) Field of Classification Search
CPC .. A61F 2/962; A61F 2/966; A61F 2/95; A61F 2002/0072; A61F 2002/2484;
(Continued)

(56) References Cited

U.S. PATENT DOCUMENTS 5,324,263 A * 6/1994 Kraus et al. ............... 604/96.01
5,484,444 A    1/1996 Braunschweiler et al.
(Continued)

FOREIGN PATENT DOCUMENTS

EP    0 875 216 A2    11/1998
EP    1 872 741 A1    1/2008
(Continued)

OTHER PUBLICATIONS

Rapra Technology Limited, Pharmaceutical Polymers 2007 Conference Proceedings Series, iSmithers Rapra Publishing, 2007, pp. 27-31.*

(Continued)

*Primary Examiner* — Eric Rosen
*Assistant Examiner* — George J. Ulsh
(74) *Attorney, Agent, or Firm* — Buchanan Ingersoll & Rooney PC

(57) ABSTRACT

A stent delivery system wherein, in a gap between an inner tube body and an outer tube body, a sealing member is arranged on the proximal side relative to a distal opening of a lumen, which extends from the proximal end of the inner tube body, and a guide wire leading-out hole. The inner circumferential surface of the sealing member is fixed to the outer circumferential surface of a first proximal tube of the inner tube body, and the outer circumferential surface of the sealing member is in sliding contact with the inner circumferential surface of a second proximal tube of the outer tube body. When blood or the like enters into the stent delivery system via the distal ends of the inner tube body and the outer tube body, progress of the blood or the like toward an operating unit side is inhibited by the sealing member.

17 Claims, 9 Drawing Sheets

(58) Field of Classification Search
CPC . A61F 2/2466; A61F 2002/011; A61M 25/00; A61M 25/0026; A61M 2025/018; A61M 25/09; A61M 25/1025
USPC .............................................. 623/1.11–1.15
See application file for complete search history.

(56) References Cited

U.S. PATENT DOCUMENTS

| | | | |
|---|---|---|---|
| 2002/0058951 A1* | 5/2002 | Fiedler ..................... | 606/108 |
| 2006/0259124 A1 | 11/2006 | Matsuoka et al. | |
| 2007/0073387 A1* | 3/2007 | Forster et al. ............... | 623/1.24 |
| 2009/0157160 A1* | 6/2009 | Van Der Leest et al. ... | 623/1.11 |
| 2010/0076541 A1* | 3/2010 | Kumoyama ................ | 623/1.11 |

FOREIGN PATENT DOCUMENTS

| | | |
|---|---|---|
| EP | 2 143 404 A1 | 1/2010 |
| JP | 6-197985 A | 7/1994 |
| JP | 2006-271565 A | 10/2006 |
| JP | 2010-517735 A | 5/2010 |
| WO | 2005/070339 A1 | 8/2005 |
| WO | 2006/138027 A2 | 12/2006 |
| WO | 2010/096708 A1 | 8/2010 |

OTHER PUBLICATIONS

Office Action (Notification of First Office Action) issued on Feb. 10, 2015, by the Chinese Patent Office in corresponding Chinese Patent Application No. 201280004075.6, and an English Translation of the Office Action. (13 pages).
*International Search Report (PCT/ISA/210) mailed on May 1, 2012, by the Japanese Patent Office as the International Searching Authority for International Application No. PCT/JP2012/051296.
The extended European Search Report issued on Oct. 15, 2014, by the European Patent Office in corresponding European Patent Application No. 12764790.7-1651. (7 pages).
Communication pursuant to Article 94(3) EPC issued on May 19, 2016, by the European Patent Office in corresponding European Patent Application No. 12 764 790.7 (3 pages).
Communication pursuant to Article 94(3) EPC issued on Oct. 16, 2015, by the European Patent Office in corresponding European Patent Application No. 12 764 790.7 (4 pages).

* cited by examiner

STENT DELIVERY SYSTEM

CROSS REFERENCE TO RELATED APPLICATIONS

This application is a continuation of International Application No. PCT/JP2012/051296 filed on Jan. 23, 2012, and claims priority to Japanese Application No. 2011-066847 filed on Mar. 25, 2011, the entire content of both of which is incorporated herein by reference.

TECHNICAL FIELD

The present invention generally relates to a stent delivery system for delivering and indwelling a stent into a living body lumen such as a blood vessel.

BACKGROUND DISCUSSION

Conventionally, there have been cases where a stent which is formed in the shape of a hollow cylinder having a multiplicity of openings in its side wall, which is made from metallic wire or the like, and which can be expanded in a living body lumen, such as blood vessel, bile duct, trachea, esophagus, urethra, etc., is used for improvement of a lesion part (stenosed part or obliterated part) generated in the living body lumen.

For example, a stent having a self-expanding function (self-expandable stent) is delivered into a living body lumen while being held in a distal portion of a delivery catheter having an outer tube disposed in the periphery of an inner tube, in the state of being compressed and contained in the gap between the inner tube and the outer tube. Then, the outer tube is retracted proximally to cause the stent to be released and expanded, whereby the stent can be put indwelling in a desired part in the living body lumen.

Such a stent delivery system having a stent and a catheter is disclosed, for example, in JP-T-2010-517735, wherein an outer tube is disposed in the periphery of an inner tube, and a stent is disposed in the state of being contained in a gap between the inner tube and the outer tube in the vicinity of a distal portion of the stent delivery system. In this system, by operating an operating unit at the proximal end, the outer tube is withdrawn toward the proximal side, whereby the stent on the distal side is smoothly released into and expanded in the living body lumen.

In the stent delivery system described in JP-T-2010-517735 mentioned above, at the time when the distal ends of the inner tube and the outer tube are advanced into the living body lumen such as a blood vessel, the blood or a contrast agent used for imaging of the inside of the living body lumen may penetrate toward the proximal side of the stent delivery system via the inner tube and the outer tube. If such blood or contrast agent having a viscosity stagnates in the gap between the inner tube and the outer tube, it may cause a sliding resistance at the time of movement of the outer tube for releasing the stent, thereby making it impossible to smoothly perform the stent indwelling operation. In addition, there is a fear that the blood or contrast agent could flow through the gap between the inner tube and the outer tube into an operating unit, thereby obstructing the operation of the operating unit.

SUMMARY

According to the disclosure herein, there is provided a stent delivery system including: an inner tube opening at a proximal end thereof; a stent which is disposed on an outer surface of a distal portion of the inner tube while being compressed toward a center axis thereof at the time of insertion into a living body lumen and which can be restored into its pre-compression shape by expanding outward when put indwelling in the living body lumen; and an outer tube which, by being disposed on an outer surface side of the inner tube, can contain the stent in its lumen and which, by moving proximally relative to the inner tube, can release the stent contained therewithin, A sealing member is provided between the outer tube and the inner tube on a proximal side relative to the stent, and the inner tube is provided, between the sealing member and the stent, with a first opening through which a lumen of the inner tube and the exterior of the inner tube communicate with each other.

According to a further aspect of the disclosure, in the stent delivery system for putting a stent indwelling in a living body lumen, the sealing member is provided between the outer tube capable of containing the stent in its lumen and the inner tube provided inside the outer tube, at a position on the proximal side relative to the stent. In addition, the inner tube is opening at the proximal end thereof, and it is provided, at a position between the sealing member and the stent, with the opening (first opening) through which the lumen of the inner tube and the exterior of the inner tube communicate with each other.

There may be a case wherein, for example, at the time of advancing the inner tube and the outer tube into the living body lumen or at the time of releasing the stent, blood or a contrast agent or the like present in the living body lumen would penetrate toward the proximal side via the inner tube or via the gap between the inner tube and the outer tube. Even in such a case, the stent delivery system as disclosed herein ensures that the flow of blood or the like toward the proximal side, especially flow into the operating unit at the proximal end, is inhibited by the sealing member. In addition, the liquid such as physiological saline injected via the opening at the proximal end of the inner tube into the lumen is caused to enter the gap between the inner tube and the outer tube through the first opening, wherein the blood or contrast agent or the like stagnating in the gap between the inner tube and the outer tube can be washed away toward the distal side.

As a result, a situation is avoided in which the blood or the like penetrating the inner tube and the outer tube from inside the living body lumen reaches the proximal side and thereby obstructs the operation of the operating part. In addition, resistance against outer tube movement which might be generated when the blood or the like stagnates in the gap between the inner tube and the outer tube is obviated. In any case, therefore, the outer tube can be smoothly moved in relation to the inner tube.

BRIEF DESCRIPTION OF DRAWINGS

The accompanying drawings are included in the specification and form a part of the disclosure here, and are used to disclose aspects and principles of the disclosure here together with the detailed description set forth below.

DETAILED DESCRIPTION

Figure 1:
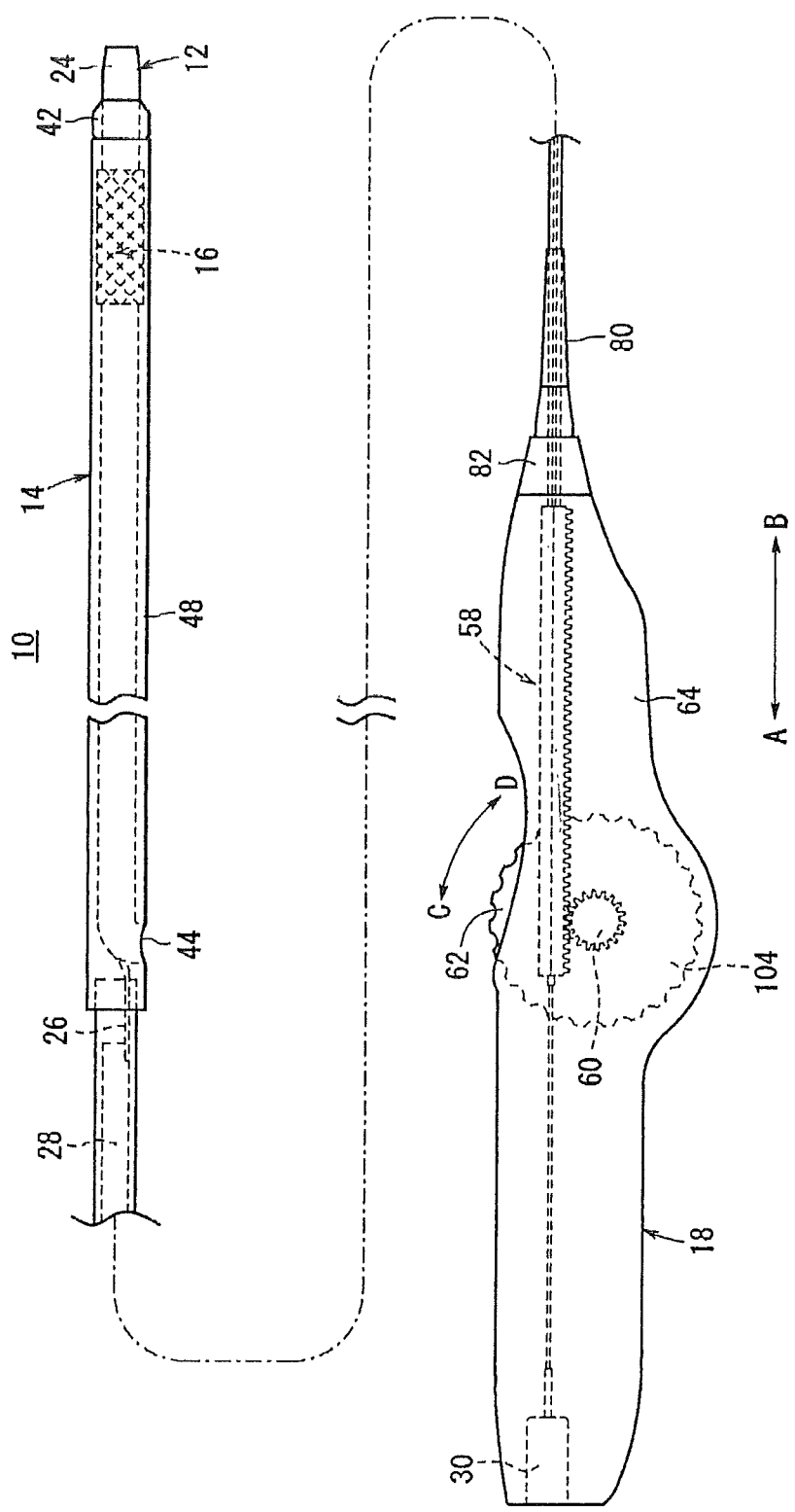
FIG. 1 is a general configuration view of a stent delivery system according to an exemplary embodiment of the disclosure.

In FIG. 1, reference sign 10 denotes a stent delivery system according to one embodiment disclosed here by way of example.

As shown in FIG. 1, the stent delivery system 10 includes: an inner tube body (inner tube) 12 formed in a tubular shape; an outer tube body (outer tube) 14 provided on the outer circumference side of the inner tube body 12; an expandable stent 16 contained between the inner tube body 12 and the outer tube body 14; and an operating unit 18 for moving the outer tube body 14 in relation to the inner tube body 12.

Merely for ease of understanding, in FIG. 1, the left side of the inner tube body 12 and the outer tube body 14 is referred to as "proximal end (rear end)" side (direction of arrow A), and the right side of the inner tube body 12 and the outer tube body 14 is referred to as "distal end" side (the direction of arrow B), the same applying also to the other figures.

As shown in FIGS. 1 to 4, the inner tube body 12 includes: a first distal tube 24 formed therein with a guide wire lumen 22 into which a guide wire 20 is inserted and passed (see FIG. 2); a first proximal tube 28 connected to the proximal side (the direction of arrow A) of the first distal tube 24 through a connecting member 26; and a connector 30 connected to the proximal end of the first proximal tube 28. The disclosed embodiment of the inner tube body 12 has a structure wherein the distal ends and the proximal ends of the first distal tube 24 and the first proximal tube 28 are both open, and the inner tube body 12 is disposed so that the distal end of the first distal tube 24 protrudes beyond the distal end of the outer tube body 14. Incidentally, the above-mentioned guide wire 20 is used, for example, for guiding the stent delivery system 10 to a lesion part in a living body lumen.

The inner tube body 12 has a structure wherein the proximal end of the first distal tube 24 and the distal end of the first proximal tube 28 are connected to each other through the connecting member 26, inside the outer tube body 14. In addition, the first proximal tube 28 has a lumen 32 penetrating therethrough from the distal end to the proximal end thereof. A liquid such as physiological saline may be injected into the lumen 32 via the connector 30. The liquid injected into the lumen 32 enters the exterior of the inner tube body 12, specifically, a gap 110 between the first proximal tube 28 and a second proximal tube 50, or a gap 108 between the first distal tube 24 and a second distal tube 48, or the like, through a distal opening (first opening 28a) of the first proximal tube 28.

It is preferable that the first distal tube 24 is formed from a highly flexible resin material, and the first proximal tube 28 from a high-strength metallic material.

The first distal tube 24 is provided with a stent holding mechanism 34 which restricts movement of the stent 16 in the axial direction.

The stent holding mechanism 34 includes a stent locking part 36 and a stent engaging part 40. The stent locking part 36 is provided at a position located on the proximal side (the direction of arrow A) of the stent 16 when the stent 16 is contained within the interior of the outer tube body 14. The stent engaging part 40 is provided on the distal side of the first distal tube 24 (the direction of arrow B) relative to the stent locking part 36, and a reduced diameter section 38 of the stent 16 to be described later is engaged with the stent engaging part 40.

Preferably, the height of the stent engaging part 40 is set smaller than the height of the stent locking part 36. This ensures that in a state wherein the stent 16 is contained inside the outer tube body 14, its proximal end makes contact with the stent locking part 36, and the reduced diameter section 38 is retained between the stent locking part 36 and the stent engaging part 40, whereby the stent 16 is retained in such a position so as not to be exposed to the exterior through the distal end of the outer tube body 14. At the time when the stent 16 is released via the distal end of the outer tube body 14, the proximal end of the stent 16 makes contact with the stent locking part 36, whereby the stent 16 is expanded in the state of being positioned in a predetermined position. In addition, at the time when the stent 16 having been released to an intermediate extent is re-contained within the inside of the outer tube body 14, the reduced diameter section 38 makes contact with the stent engaging part 40, whereby the stent 16 is retained in a predetermined position.

At the distal end of the first distal tube 24, there is formed a stopper part 42 which bulges radially outward and which restricts movement of the outer tube body 14 in the distal direction. This ensures that the outer tube body 14 is inhibited from protruding in the axial direction (in the direction of arrow B) relative to the distal end of the inner tube body 12.

In addition, the proximal end of the first distal tube 24 is gently curved toward the radially outer side of the first distal tube 24 so that it can communicate with a guide wire leading-out hole (opening) 44 of the outer tube body 14, as described below.

On the outer circumferential surface of the first proximal tube 28, there is formed a sealing member 46 which is formed, for example, of a metallic material, a resin material or a high-viscosity liquid (e.g., ointment such a vaseline, or silicone oil) in an annular shape with a rectangular sectional shape. The inner circumferential surface of the sealing member 46 is fixed to the outer circumferential surface of the first proximal tube 28 by an adhesive or the like.

In the case where the sealing member 46 is formed of an elastic material (e.g., a resin material), the outside diameter of the sealing member 46 is set to be approximately equal to or a little greater than the inside diameter of the outer tube body 14 so that the sealing member 46 makes sliding contact with the inner circumferential surface of the outer tube body 14. More specifically, the outside diameter of the sealing member 46 is preferably about 0.5-5% greater than the inside diameter of the outer tube body 14.

On the other hand, in the case where the sealing member 46 is formed of a non-elastic material (e.g., a metallic material), the outside diameter of the sealing member 46 is set to be slightly smaller than the inside diameter of the outer tube body 14 so that a minute clearance is provided between the outer tube body 14 and the sealing member 46.

A resin material suitable for forming the sealing member 46 may be, for example, a water-swellable resin material which is increased in volume by absorbing water content such as blood or the like. In such a case, the outside diameter of the sealing member 46 before swelling with water content is set to be smaller than the inside diameter of the outer tube body 14.

Hence, by virtue of the sealing member 46, the gap between the inner tube body 12 and the outer tube body 14 is retained in a liquid-tight manner.

The outer tube body 14 is composed of tubular bodies; specifically, it includes the second distal tube 48 in which the first distal tube 24 of the inner tube body 12 is disposed, and the second proximal tube 50 which is connected to the proximal side (the direction of arrow A) of the second distal tube 48 and in which the first proximal tube 28 is disposed. The distal end of the second distal tube 48 functions as a release port at the time of putting the stent 16 indwelling in a lesion part in a living body lumen, and functions also as a containing port at the time of re-containing the stent 16 which has been released to an intermediate extent.

In addition, on the proximal end of the second distal tube 48 (between the first opening 28a and the stent 16), there is formed the guide wire leading-out hole 44 through which the lumen of the second distal tube 48 and the exterior of the second distal tube 48 communicate with each other. The guide wire leading-out hole 44 is provided so that it can communicate with the opening of the guide wire lumen 22 of the first distal tube 24 provided inside the second distal tube 48. Through the guide wire leading-out hole 44, the guide wire 20 is passed and inserted into the guide wire lumen 22 of the inner tube body 12.

The guide wire leading-out hole 44 also functions as a discharge hole for discharging to the exterior any liquid that may have been forced to flow from the connector 30 through the lumen 32 and the first opening 28a.

At a distal portion of the second distal tube 48, a contrast marker 52 is provided on the outer circumferential surface of the second distal tube 48. The contrast marker 52 is formed in an annular shape from a radiopaque material, for example.

Figure 3:
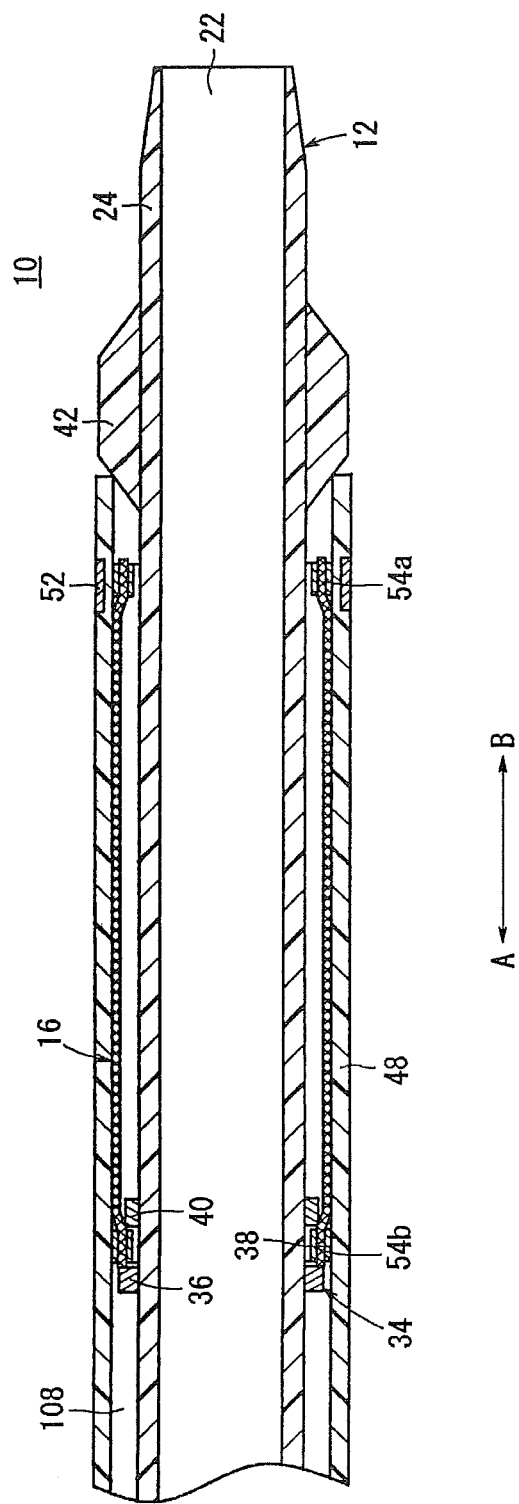
FIG. 3 is an enlarged sectional view showing the vicinity of distal ends of the inner tube body and the outer tube body of FIG. 2.
Figure 4:
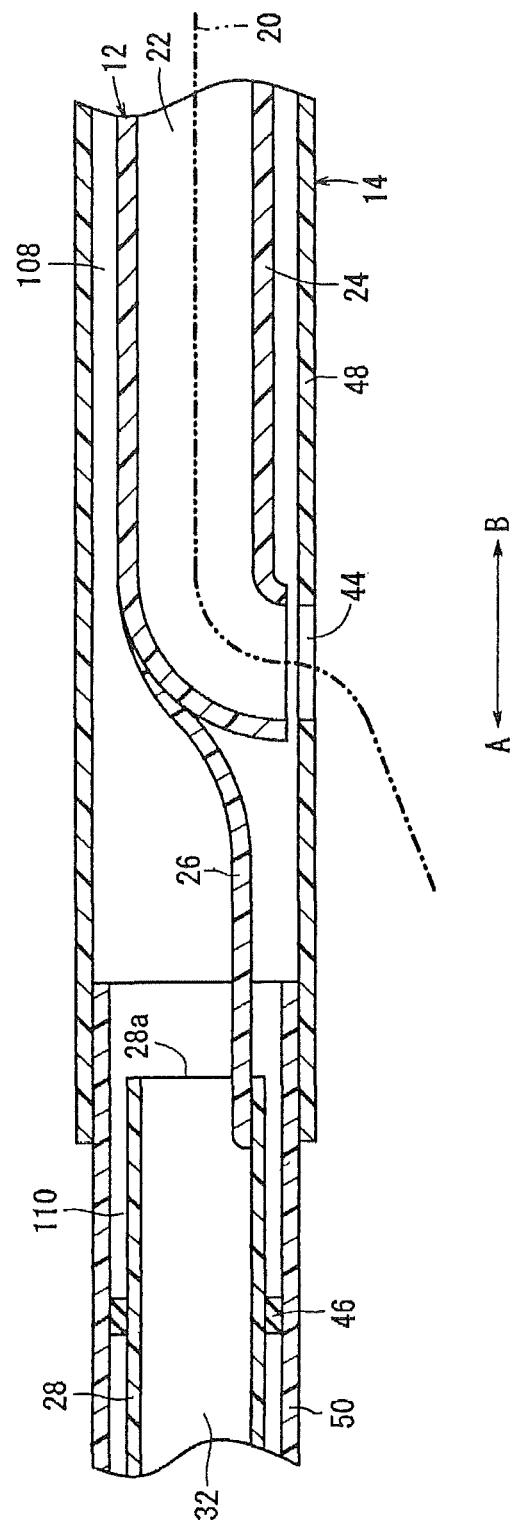
FIG. 4 is an enlarged sectional view of the inner tube body and the outer tube body, showing the vicinity of a guide wire leading-out hole shown in FIG. 2.
Figure 5:
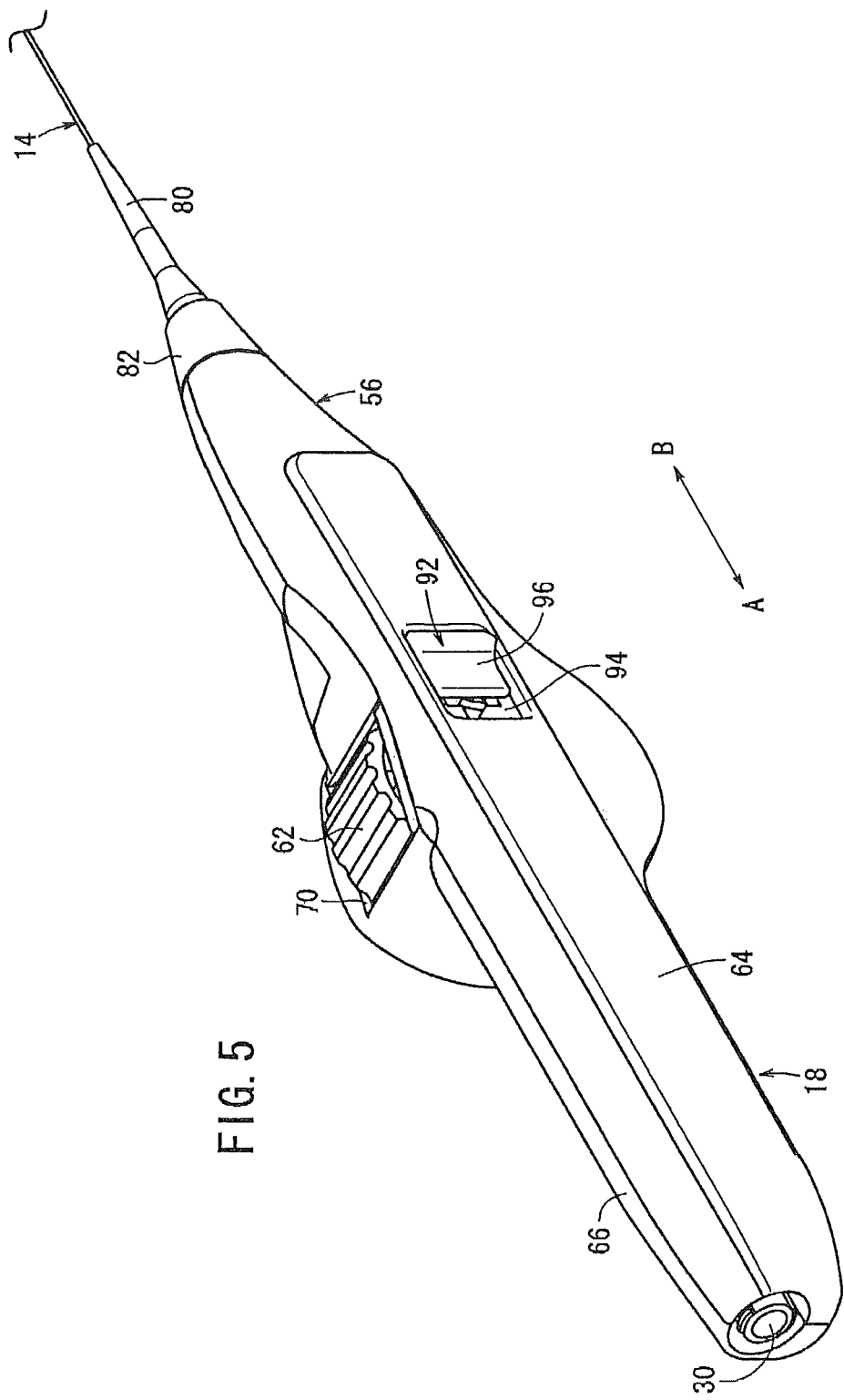
FIG. 5 is an external appearance perspective view of an operating unit including the stent delivery system shown in FIG. 1.
Figure 6:
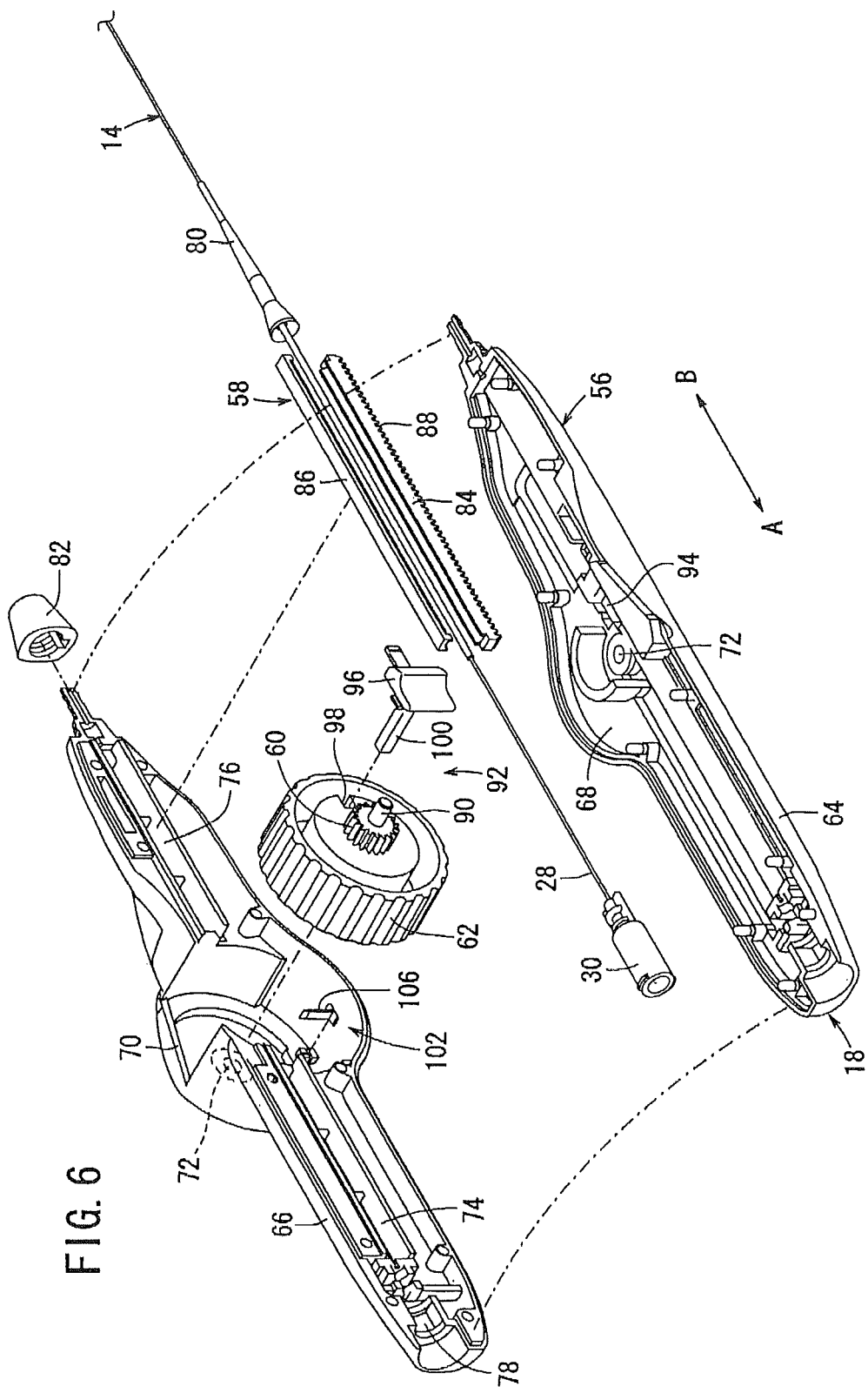
FIG. 6 is an exploded perspective view of the operating unit shown in FIG. 5.

As shown in FIG. 3, the stent 16 is formed in the shape of a substantially cylindrical mesh having a multiplicity of openings. The stent 16 is preferably a self-expandable stent which is disposed inside the second distal tube 48 of the outer tube body 14 in the state of being compressed radially inward, namely, toward the center axis at the time of insertion into a living body lumen, and which, by being released via the distal end of the outer tube body 14 into a lesion part in the living body lumen, can be expanded radially outward to be restored into its pre-compression shape. The material constituting the stent 16 is preferably a superelastic alloy such as Ni—Ti alloy, for example.

At the distal end and the proximal end of the stent 16, there are provided contrast markers 54a, 54b preferably formed in an annular shape from a radiopaque material, for example. In addition, the reduced diameter section 38 whose diameter is reduced radially inward is formed at the proximal end of the stent 16.

As shown in FIGS. 1 and 5 to 7, the operating unit 18 includes: a housing 56; a rack member 58 contained inside the housing 56 and connected to the outer tube body 14; and a rotary roller 62 which has a first gear 60 meshed with the rack member 58 and by which the rack member 58 is displaced rectilinearly (that is, along the axis of the housing 56).

The housing 56 includes a rounded area at its central portion, and is composed of a first housing 64 and a second housing 66 into which the housing 56 is bisected at the center in the thickness direction thereof. The housing 56 is provided, inside the first and second housings 64 and 66, with a roller containing section 68 capable of containing the rotary roller 62 in a roughly central portion thereof. A part of the rotary roller 62 is exposed to the exterior through a roller hole 70 formed in the roller containing section 68.

In addition, the rotary roller 62 is rotatably supported by a pair of bearings 72 formed at inner wall surfaces of the first and second housings 64 and 66.

The second housing 66 includes therein first and second containing grooves 74 and 76 in which the rack member 58 is contained and retained so as to be movable in the axial direction (in the directions of arrows A, B). The first containing groove 74 is provided on the proximal side (the direction of arrow A) in the second housing 66, while the second containing groove 76 is provided on the distal side (the direction of arrow B) in the second housing 66. The roller containing section 68 is disposed between the first containing groove 74 and the second containing groove 76.

With the first housing 64 and the second housing 66 secured together to form housing 56, the rack member 58 is retained by the first and second containing grooves 74 and 76 in the state of being movable rectilinearly toward the distal side and the proximal side.

A connector containing section 78 configured to contain the connector 30 is formed on the proximal side (the direction of arrow A) of the first containing groove 74. The connector 30 is fixed to the housing 56 since it is contained in the connector containing section 78. As a result, the proximal end of the first proximal tube 28 forming the inner tube body 12 is fixed to the operating unit 18 through the connector 30.

The connector containing section 78 opens toward the proximal side (the direction of arrow A) of the housing 56, and is formed so that a liquid injector (not shown) can be connected to the connector 30 from the exterior of the housing 56.

A distal nozzle 80 by which the second proximal tube 50 of the outer tube body 14 is slidably retained is mounted to the distal end of the housing 56. The distal nozzle 80 is formed therein with a through-hole (not shown), through which the second proximal tube 50 is inserted and passed. When the distal nozzle 80 is mounted to the distal end of the housing 56, a cap 82 is screw engaged onto the distal end of the housing 56, whereby the distal nozzle 80 is thus fixed.

The rack member 58 is composed of a pair of first and second block bodies 84 and 86 which are formed in straight and substantially symmetric shapes. The proximal end of the second proximal tube 50 of the outer tube body 14 is fixed by being clamped between the first block body 84 and the second block body 86.

The rack member 58 composed of the first and second block bodies 84 and 86 is inserted in the first and second containing grooves 74 and 76 inside the housing 56, such that the rack member 58 is retained in a state where it is axially movable toward the distal side and the proximal side of the housing 56.

In addition, the first block body 84 is provided inside the housing 56 so as to face the rotary roller 62, and its side surface facing the rotary roller 62 is provided with a plurality of tooth portions 88 defined by projections and recesses arranged along the axial direction (the direction of arrows A, B).

The rotary roller 62 is provided at its center with a pair of rotary shafts 90 projecting in mutually opposing directions. The rotary shafts 90 are inserted in the bearings 72 of the first and second housings 64 and 66, respectively.

A first gear 60 facing radially outward, with the rotary shaft 90 as a center, is provided at a side surface of the rotary roller 62, and is meshed with the tooth portions 88 of the rack member 58. With the rotary roller 62 rotated, the rack member 58 is moved rectilinearly along the first and second containing grooves 74 and 76.

A part of an outer circumferential portion of the rotary roller 62 is exposed to the exterior through the roller hole 70, and the operator rotates the rotary roller 62 through the exposed part.

Figure 7:
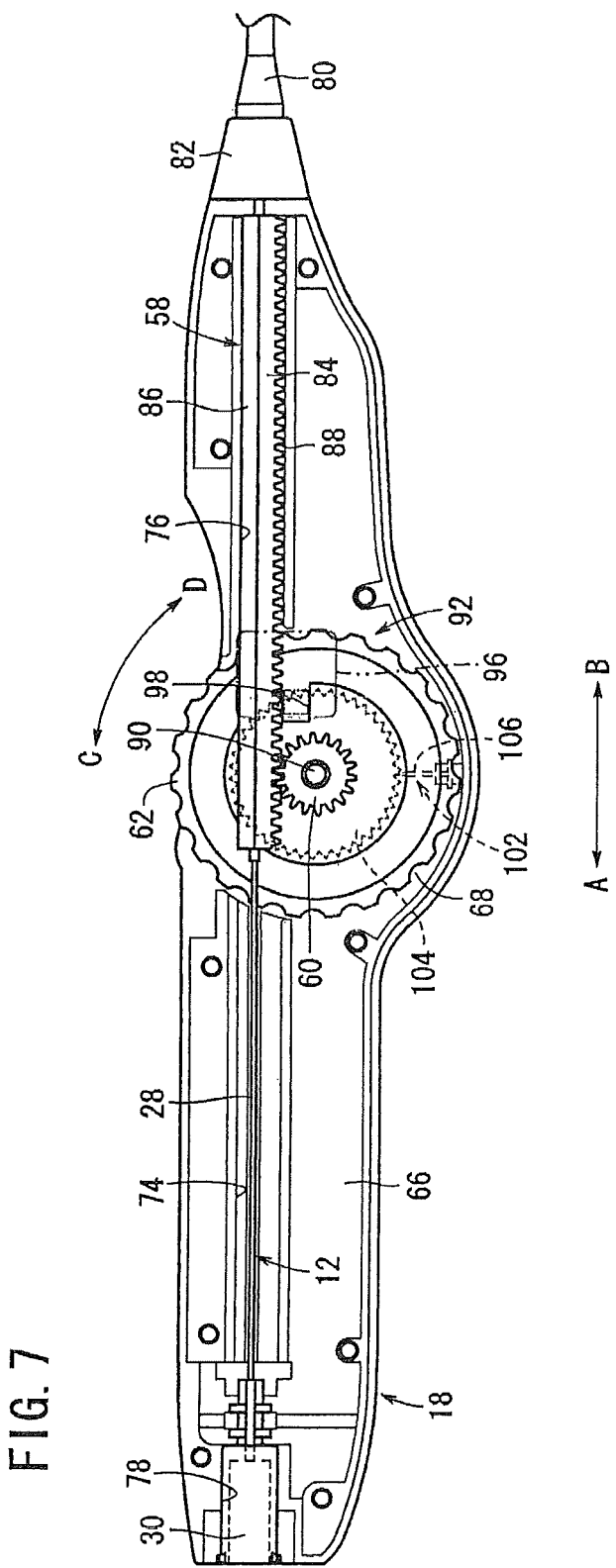
FIG. 7 is a side view of an inside of the operating unit shown in FIGS. 5 and 6.

In the above-mentioned operating unit 18, for example, the operator rotates the rotary roller 62 in a predetermined direction (in the direction of arrow C) relative to the housing 56, as shown in FIG. 7. By this operation, the rack member 58 inside the housing 56 is moved along the first and second containing grooves 74 and 76 toward the connector 30 side (in the direction of arrow A), attended by movement (retraction) of the outer tube body 14 toward the proximal side of the housing 56. As a result, the stent 16 is released via the distal end of the outer tube body 14.

On the other hand, when the rotary roller 62 is rotated in the opposite direction to the above-mentioned (in the direction of arrow D) after the stent 16 is released to an intermediate extent, the rack member 58 is moved along the first and second containing grooves 74 and 76 in the direction for spacing away from the connector 30 (in the direction of arrow B). This is attended by movement (advancement) of the outer tube body 14 toward the distal side relative to the inner tube body 12, whereby the stent 16 is re-contained within the inside of the outer tube body 14.

As shown in FIG. 7, the operating unit 18 is provided with a locking mechanism 92 by which a moving motion of the rack member 58 can be restricted through restriction of a rotating motion of the rotary roller 62.

The locking mechanism 92 is composed of: a slide member 96 which is provided at a hole part 94 opening in a side surface of the first housing 64 so that it can be displaceable by sliding; and a pin groove 98 formed in a side surface of the rotary roller 62 so as to face the slide member 96. The slide member 96 is retained so as to be rectilinearly displaceable toward the distal and proximal sides (in the directions of arrows A, B) of the first housing 64 through the hole part 94. When a pin 100 rectangular in sectional shape projecting into the inside of the first housing 64 is inserted into the pin groove 98 of the rotary roller 62, in the condition where the slide member 96 is located on the proximal side in the housing 56, a rotating motion of the rotary roller 62 is restricted.

In addition, with the slide member 96 moved toward the distal side of the housing 56, the pin 100 is disengaged from the pin groove 98 toward the radially outer side of the rotary roller 62. Therefore, the restriction of the rotation of the rotary roller 62 by the pin 100 is removed, resulting in a state wherein the rack member 58 can be moved in the axial direction (in the directions of arrows A, B) under the rotating action of the rotary roller 62.

The operating unit 18 is also provided with an intermittent mechanism 102 for putting the rotary roller 62 into intermittent rotation. The intermittent mechanism 102 includes: a second gear 104 provided at a side surface, opposite to the first gear 60, of the rotary roller 62; and a notch member 106 retained by the second housing 66 and engaged with the tooth portion of the second gear 104. When the rotary roller 62 is rotated, the notch member 106 engaged with the second gear 104 is elastically deformed, to be disengaged from a recess of the tooth portion and come over a projection, thereby being again engaged with another recess. This enables an intermittent rotating motion. Furthermore, from a sound generated at the moment of engagement between the notch member 106 and the second gear 104, it is also possible to confirm the rotating motion and/or a rotational angle of the rotary roller 62.

The stent delivery system 10 according to exemplary embodiment disclosed here is basically configured as above-described. The operation and effect of the stent delivery system 10 will be described below. Incidentally, a state is assumed in which the guide wire 20 is inserted in a living body lumen (for example, a blood vessel), and its distal end has preliminarily been set indwelling in a lesion part in the living body lumen.

In such a preparatory state, flushing of the stent delivery system 10 shown in FIG. 1 is conducted. First, the operator connects a liquid injector (not shown) to the connector 30 provided at the proximal end of the operating unit 18, and injects a liquid from the liquid injector into the connector 30. As a result, the liquid is distributed to the distal side of the inner tube body 12 and the outer tube body 14 (in the direction of arrow B).

Then, the liquid having reached the distal ends are ejected from the distal ends of the inner tube body 12 and the outer tube body 14, whereby flushing of the inside of the inner tube body 12 and the outer tube body 14 is completed in the exterior of a living body.

Figure 2:
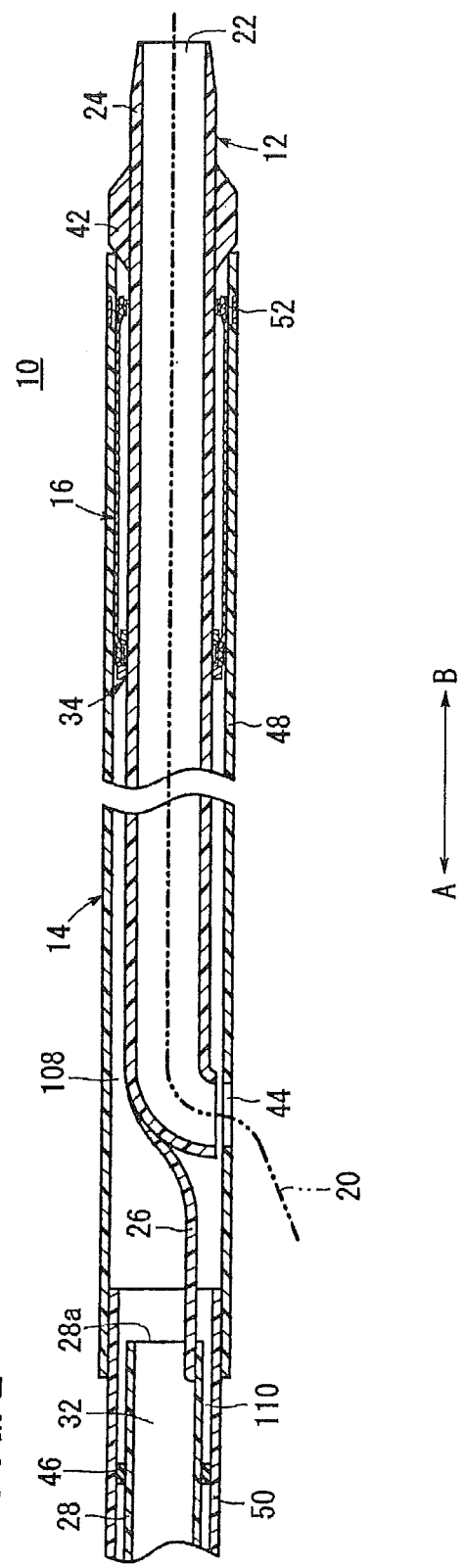
FIG. 2 is a partially omitted sectional view showing an inner tube body and an outer tube body in the stent delivery system of FIG. 1.

Next, as shown in FIG. 2, the proximal end of the guide wire 20 exposed to the exterior of the living body is inserted and passed via the distal end of the inner tube body 12 into the guide wire lumen 22, and the inner tube body 12 and the outer tube body 14 are gradually advanced along the guide wire 20 into a living body lumen. The proximal end of the guide wire 20 is led out to the exterior of the outer tube body 14 by way of the guide wire leading-out hole 44.

After the arrival of the distal end of the outer tube body 14 in a lesion part is confirmed by the contrast marker 52, the slide member 96 of the operating unit 18 is moved toward the distal side (in the direction of arrow B), and the pin 100 is disengaged from the pin groove 98 of the rotary roller 62, whereby the restriction of the rotation of the rotary roller 62 is removed. Then, the rotary roller 62 is rotated in a predetermined direction (in the direction of arrow C).

Figure 8:
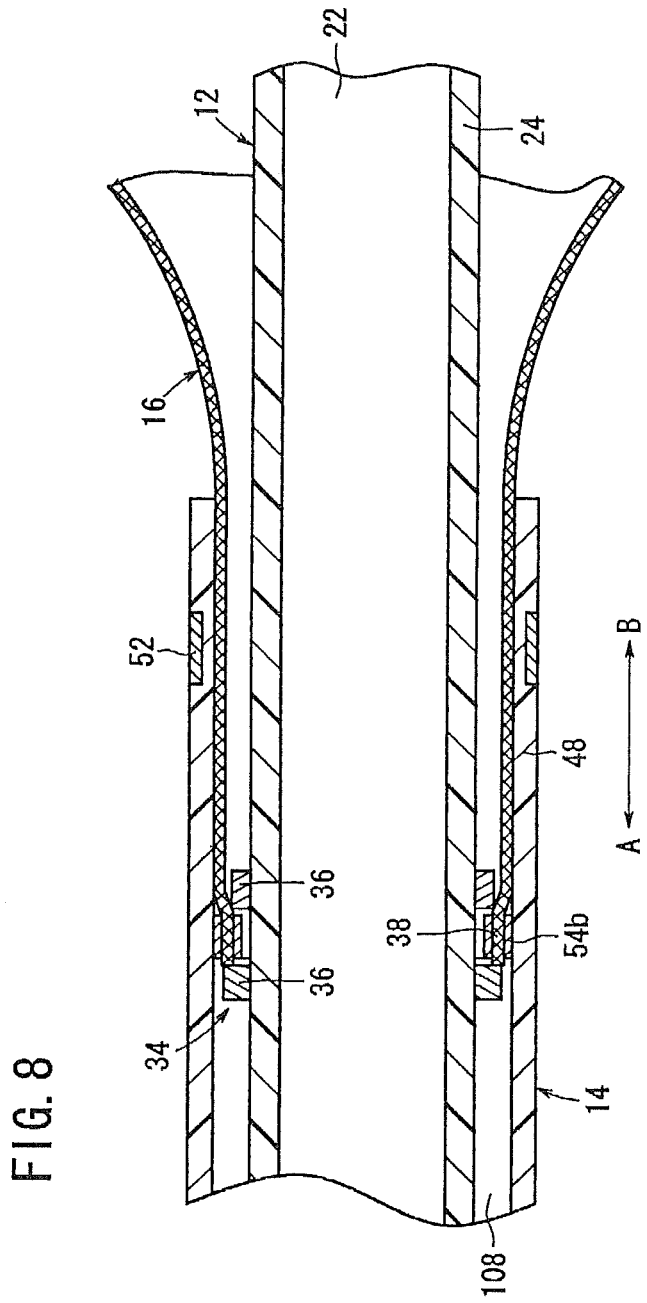
FIG. 8 is an enlarged sectional view showing a state in which a stent is released via the distal end of the outer tube body to an intermediate extent or a case of re-containing the stent which has been released to an intermediate extent into the inside of the outer tube body.

As a result, based on the rotation of the first gear 60, the rack member 58 is moved proximally (in the direction of arrow A) within the housing 56. This is attended by gradual movement of the outer tube body 14 toward the proximal side of the operating unit 18. As a result, as shown in FIG. 8, the stent 16 contained in the outer tube body 14 starts being gradually exposed, starting from its distal portion; simultaneously, the stent 16 starts being expanded radially outward. Then, the stent 16 comes into the state of being completely exposed from the outer tube body 14, whereby the stent 16 is set indwelling in the lesion part in the state of being expanded in a cylindrical shape.

In this case, based on the advancement of the inner tube body 12 and the outer tube body 14 into the living body lumen or on the expansion of the stent 16, blood or a contrast agent or the like in the living body lumen may enter into the inside of the stent delivery system 10 via the distal ends of the inner tube body 12 and the outer tube body 14 or via the guide wire leading-out hole 44, to be distributed toward the proximal side (in the direction of arrow A) through the guide wire lumen 22 and the gaps 108 and 110 between the inner tube body 12 and the outer tube body 14. Even in such a situation, however, distribution of the blood or the contrast agent or the like to the operating unit 18 side (in the direction of arrow A) is securely inhibited by the sealing member 46 provided in the gap 110 between the inner tube body 12 (the first proximal tube 28) and the outer tube body 14 (the second proximal tube 50).

Further, a liquid such as physiological saline is injected through the connector 30 into the lumen 32 of the inner tube body 12 (the first proximal tube 28). This ensures that the liquid flows through the first opening 28a into the gaps 108 and 110 and the like, whereby the blood or the contrast agent or the like stagnating in the gaps 108 and 110 and the like is washed away toward the distal side. The blood or the contrast agent or the like thus washed away is favorably ejected to the exterior by way of the guide wire leading-out hole 44 and the distal opening of the outer tube body 14 (the second proximal tube 50). Preferably, the sectional area of the gap 110 is set to be smaller than the sectional area of the first opening 18a.

As a result of the above-described operation, the blood or the contrast agent or the like having entered through the distal ends of the inner tube body 12 and the outer tube body 14 is securely inhibited from advancing toward the operating unit 18 side (in the direction of arrow A), and, hence, inhibited from obstructing the operation of the operating unit 18.

Finally, the inner tube body 12 and the outer tube body 14 constituting the stent delivery system 10 are then withdrawn proximally (in the direction of arrow A), whereby they are removed to the exterior of the living body, with only the stent 16 left indwelling in the lesion part.

As mentioned above, in the embodiment disclosed here, for example, at the time when the inner tube body 12 and the outer tube body 14 constituting the stent delivery system 10 are advanced into the living body lumen or at the time when the stent 16 is released, the blood or the contrast agent or the like may enter into the gap between the inner tube body 12 and the outer tube body 14 via the distal end of the outer tube body 14 or via the guide wire leading-out hole 44. Even in such a situation, the blood or the like being distributed along the gaps 108 and 110 toward the proximal side (in the direction of arrow A) is prevented by the sealing member 46 from such distribution.

Consequently, the blood or the like having entered into the gaps 108 and 110 between the inner tube body 12 and the outer tube body 14 from the body lumen is inhibited from reaching the operating unit 18, and, hence, prevented from obstructing the operation of the operating unit 18.

In addition, if the blood or the contrast agent or the like should be stagnated in the gaps 108 and 110, there is a possibility that the blood or the like with viscosity might act as a resistance to movement of the outer tube body 14 in the axial direction relative to the inner tube body 12. In the above-described stent delivery system 10, however, the liquid such as physiological saline injected via the connector 30 ensures that the blood or the contrast agent or the like stagnating in the gaps 108 and 110 can be washed away toward the distal side and be securely ejected to the exterior.

In any case, therefore, the outer tube body 14 can be smoothly moved in relation to the inner tube body 12.

Furthermore, in the case where the sealing member 46 is formed of an elastic material, the sealing member 46 is in sliding contact with the inner circumferential surface of the outer tube body 14. Therefore, leakage of the blood or the contrast agent or the like through a gap between the sealing member 46 and the inner circumferential surface is prevented more assuredly.

On the other hand, in the case where the sealing member 46 is formed of a non-elastic material, there is a minute clearance between the sealing member 46 and the inner circumferential surface of the outer tube body 14. In this case, however, the blood or contrast agent or the like would not leak out to the proximal side (in the direction of arrow A) through the clearance, since the blood or contrast agent or the like has a predetermined viscosity, for example. In addition, since the sealing member 46 is not in contact with the outer tube body 14, the sealing member 46 would not act as a sliding resistance at the time of axial movement of the outer tube body 14, so that the outer tube body 14 can be smoothly moved.

While the above-mentioned sealing member 46 has been configured to be fixed to the outer circumferential surface of the first proximal tube 28 constituting the inner tube body 12, this configuration is not restrictive. For instance, the sealing member 46 may be fixed to the inner circumferential surface of the second proximal tube 50 of the outer tube body 14 by an adhesive or the like. In this case, when the sealing member 46 is formed of an elastic material, the sealing member 46 is set in sliding contact with the outer circumferential surface of the first proximal tube 28. On the other hand, when the sealing member 46 is formed of a non-elastic material, the sealing member 46 is set in a non-contact state wherein a minute clearance is left between the sealing member 46 and the outer circumferential surface.

In addition, it suffices for the sealing member 46 to be provided in a position on the proximal side (the direction of arrow A) relative to the first opening 28a of the first proximal tube 28 of the inner tube body 12 and the guide wire leading-out hole 44 of the second distal tube 48 of the outer tube body 14.

Figure 9:
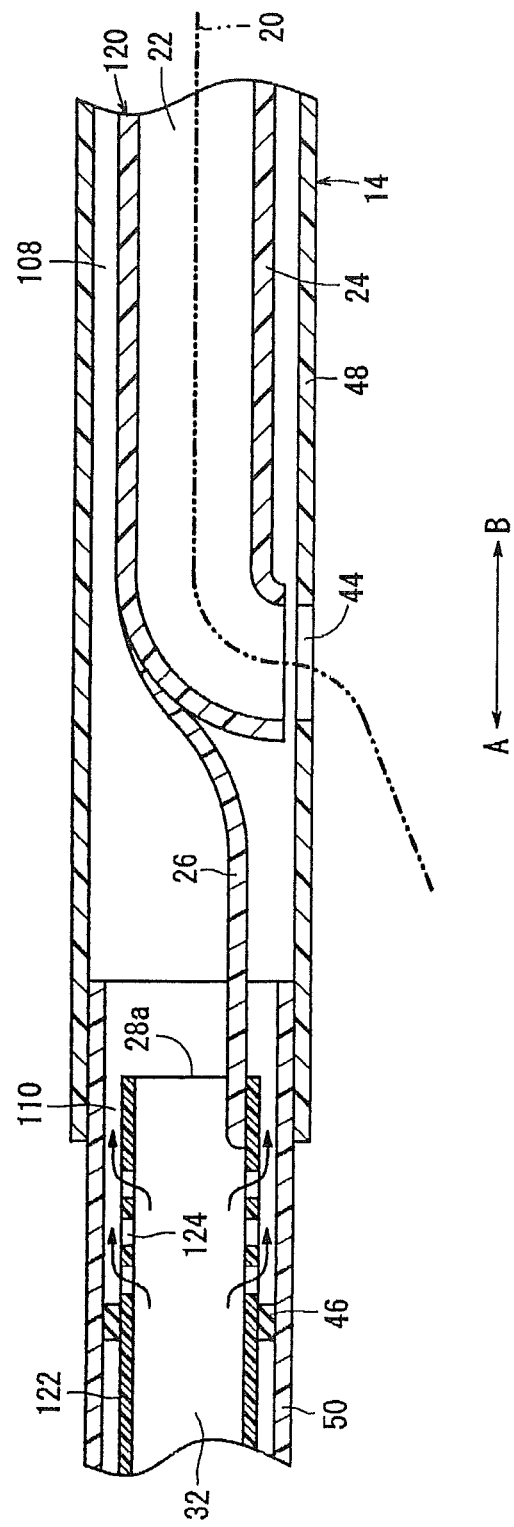
FIG. 9 is an enlarged sectional view of the vicinity of a guide wire leading-out hole in application of an inner tube body according to a further exemplary embodiment of the disclosure.

As shown in FIG. 9, the first proximal tube 122 of the inner tube body 120 as above-described may be provided further with a slit (a second opening) 124 at a position on the distal side (the direction of arrow B) relative to the sealing member 46 so that the outer circumference side of the first proximal tube 122 and the lumen 32 inside the first proximal tube 122 communicate with each other. This slit 124 is formed, for example, in a spiral shape in relation to the axis of the inner tube body 120.

The area (surface area) of the slit 124 is preferably set to be large in relation to the sectional area of the gap 110. That is, the area (surface area) of the slit is larger than the sectional area of the gap 110. More specifically, the area (surface area) of the slit is preferably about 1.1-3.0 times as large as the sectional area of the gap.

Further, instead of providing the spiral slit 124, a plurality of communicating holes may be provided which are mutually spaced apart along the axial direction of the first proximal tube 122. In this case, also, the total area (total surface area) of the plurality of communicating holes is preferably set to be large in relation to the sectional area of the gap 110.

With such a slit or slits 124 provided, the liquid such as physiological saline injected through the connector 30 into the lumen 32 of the inner tube body 120 (the first proximal tube 122) is caused to assuredly flow into the gap 110 between the first proximal tube 122 and the second proximal tube 50 through the slit or slits 124. Therefore, a situation in which the blood or contrast agent or the like remains in the gap 110 between the first proximal tube 122 and the second proximal tube 50 and coagulated there is securely avoided. Consequently, a situation in which the blood or contrast agent or the like remaining in the gap causes an increased sliding resistance at the time of movement of the outer tube 14 can be prevented assuredly.

The detailed description above describes a stent and stent delivery system disclosed by way of example. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
   an inner proximal tube opening at a proximal end thereof;
   an inner distal tube having a proximal side connected to the inner proximal tube by a connecting member;
   a stent which is disposed on an outer surface of the inner distal tube while being compressed toward a center axis thereof at the time of insertion into a living body lumen and which can be restored into its pre-compression shape by expanding outward when put indwelling in the living body lumen; and
   an outer tube which, by being disposed on an outer surface side of the inner distal tube, can contain the stent in its lumen and which, by moving proximally relative to the inner distal tube, can release the stent contained in its inside,
   wherein a sealing member is provided between the outer tube and the inner proximal tube on a proximal side relative to the stent, and the inner proximal tube is provided, between the sealing member and the stent, with a first opening through which a lumen of the inner proximal tube and the exterior of the inner proximal tube communicate with each other, and
   wherein said sealing member is fixed to said inner proximal tube on a proximal side relative to said first opening.

2. The stent delivery system according to the claim 1,
   wherein the outer tube is provided, between the first opening and the stent, with a hole through which a lumen of the outer tube and the exterior of the outer tube communicate with each other.

3. The stent delivery system according to claim 1,
   wherein the sealing member is in sliding contact with the outer tube.

4. The stent delivery system according to claim 1,
   wherein a sectional area of the first opening is set to be large in relation to the sectional area of a gap between the outer tube and the inner proximal tube.

5. The stent delivery system according to claim 1,
   wherein the inner proximal tube is provided, between the sealing member and the first opening, with a second opening through which the lumen of the inner proximal tube and the exterior of the inner proximal tube communicate with each other.

6. The stent delivery system according to claim 5,
   wherein the second opening is provided so as to be adjacent to the sealing member.

7. The stent delivery system according to claim 5,
   wherein the second opening is composed of a spiral slit or a plurality of mutually spaced-apart communicating holes.

8. The stent delivery system according to claim 5,
   wherein the area of the second opening is larger than the sectional area of a gap between the outer tube and the inner proximal tube.

9. The stent delivery system according to claim 1,
   wherein the sealing member
   is formed of a metallic material, a resin material, or a high-viscosity liquid.

10. A stent delivery system comprising:
    an inner proximal tube;
    an inner distal tube having a proximal side connected to the inner proximal tube by a connecting member;
    an outer tube provided on an outer circumference side of the inner distal tube, a gap defined between the inner distal tube and the outer tube being configured to contain an expandable stent;
    an operating unit connected to the inner proximal tube for moving the outer tube relative to the inner proximal tube to deploy the expandable stent; and
    a sealing member arranged between the inner proximal tube and the outer tube;
    wherein, when blood or other fluid enters into the stent delivery system via an open distal end of the inner distal tube or of the outer tube, said sealing member prevents the blood or other fluid from spreading to the operating unit,
    wherein said inner proximal tube is provided, between the sealing member and the stent, with a first opening through which a lumen of the inner proximal tube and an exterior of the inner proximal tube communicate with each other, and
    wherein said sealing member is fixed to said inner proximal tube on a proximal side relative to said first opening.

11. The stent delivery system according to claim 10,
    wherein the outer tube includes an outer distal tube and an outer proximal tube; and
    wherein an inner circumferential surface of said sealing member is fixed to the outer circumferential surface of the inner proximal tube, and an outer circumferential surface of the sealing member is in sliding contact with an inner circumferential surface of the outer proximal tube.

12. The stent delivery system according to claim 11,
    wherein the inner circumferential surface of said sealing member is fixed to the outer circumferential surface of the inner proximal tube by an adhesive.

13. The stent delivery system according to claim 10,
    wherein said sealing member is formed of a metallic material and an outer diameter of said sealing member is slightly smaller than an inner diameter of the outer tube.

14. The stent delivery system according to claim 10,
    wherein said sealing member is formed of an elastic material and an outer diameter of said sealing member is approximately equal to an inner diameter of the outer tube.

15. The stent delivery system according to claim 10,
    wherein said sealing member is formed of an elastic material and an outer diameter of said sealing member is a little greater than an inner diameter of the outer tube.

16. The stent delivery system according to claim 10, wherein said sealing member is formed from a water-swellable resin material and an outer diameter of said sealing member before swelling with water is smaller than an inner diameter of the outer tube.

17. The stent delivery system according to claim 10, wherein said sealing member is formed from a high-viscosity liquid.

\* \* \* \* \*